United States Patent
Chen et al.

(10) Patent No.: US 11,967,004 B2
(45) Date of Patent: Apr. 23, 2024

(54) DEEP LEARNING BASED IMAGE RECONSTRUCTION

(71) Applicant: Shanghai United Imaging Intelligence Co., Ltd., Shanghai (CN)

(72) Inventors: Zhang Chen, Brookline, MA (US); Shanhui Sun, Lexington, MA (US); Xiao Chen, Lexington, MA (US); Terrence Chen, Lexington, MA (US)

(73) Assignee: Shanghai United Imaging Intelligence Co., Ltd., Shanghai (CN)

(*) Notice: Subject to any disclaimer, the term of this patent is extended or adjusted under 35 U.S.C. 154(b) by 342 days.

(21) Appl. No.: 17/378,465

(22) Filed: Jul. 16, 2021

(65) Prior Publication Data

US 2023/0014745 A1    Jan. 19, 2023

(51) Int. Cl.
| | |
|---|---|
| *G06T 11/00* | (2006.01) |
| *A61B 5/00* | (2006.01) |
| *A61B 5/055* | (2006.01) |
| *G06F 18/214* | (2023.01) |
| *G06F 18/22* | (2023.01) |
| *G06K 9/62* | (2022.01) |

(Continued)

(52) U.S. Cl.
CPC ............ *G06T 11/005* (2013.01); *A61B 5/055* (2013.01); *A61B 5/7267* (2013.01); *G06F 18/214* (2023.01); *G06F 18/22* (2023.01); *G06N 3/04* (2013.01); *G06N 3/08* (2013.01); *G06T 5/50* (2013.01); *G06T 2207/10088* (2013.01); *G06T 2207/20081* (2013.01); *G06T 2207/20084* (2013.01); *G06T 2207/20221* (2013.01)

(58) Field of Classification Search
CPC .............. G06T 11/005; G06T 5/50; G06T 2207/10088; G06T 2207/20081; G06T 2207/20084; G06T 2207/20221; G06F 18/22; G06F 18/214; A61B 5/055; A61B 5/7267; G06N 3/04; G06N 3/08
See application file for complete search history.

(56) References Cited

U.S. PATENT DOCUMENTS

2019/0266761 A1* 8/2019 Malkiel .............. G01R 33/5611
2020/0294287 A1* 9/2020 Schlemper .............. G06T 7/262
(Continued)

OTHER PUBLICATIONS

Do, Won-Joon, et al. "Reconstruction of multicontrast MR images through deep learning." Medical physics 47.3 (2020): 983-997. (Year: 2020).*

(Continued)

*Primary Examiner* — Bobbak Safaipour
*Assistant Examiner* — Jongbong Nah
(74) *Attorney, Agent, or Firm* — Zhong Law LLC

(57) ABSTRACT

Disclosed herein are systems, methods, and instrumentalities associated with reconstructing magnetic resonance (MR) images based on under-sampled MR data. The MR data include 2D or 3D information, and may encompass multiple contrasts and multiple coils. The MR images are reconstructed using deep learning (DL) methods, which may accelerate the scan and/or image generation process. Challenges imposed by the large quantity of the MR data and hardware limitations are overcome by separately reconstructing MR images based on respective subsets of contrasts, coils, and/or readout segments, and then combining the reconstructed MR images to obtain desired multi-contrast results.

20 Claims, 7 Drawing Sheets

(51) Int. Cl.
    *G06N 3/04*     (2023.01)
    *G06N 3/08*     (2023.01)
    *G06T 5/50*     (2006.01)

(56) References Cited

U.S. PATENT DOCUMENTS

| | | | |
|---|---|---|---|
| 2020/0311926 A1* | 10/2020 | Tian | G06T 3/4053 |
| 2020/0319283 A1* | 10/2020 | Wang | G01R 33/5608 |
| 2021/0118203 A1* | 4/2021 | Ding | G01R 33/5614 |
| 2021/0217213 A1* | 7/2021 | Cole | G06N 3/088 |

OTHER PUBLICATIONS

Deshmane, Anagha, et al. "Parallel MR imaging." Journal of Magnetic Resonance Imaging 36.1 (2012): 55-72. (Year: 2012).*

Weng, Yu, et al. "Nas-unet: Neural architecture search for medical image segmentation." IEEE access 7 (2019): 44247-44257. (Year: 2019).*

Dar, Salman UH, et al. "Prior-guided image reconstruction for accelerated multi-contrast MRI via generative adversarial networks." IEEE Journal of Selected Topics in Signal Processing 14.6 (2020): 1072-1087. (Year: 2020).*

* cited by examiner

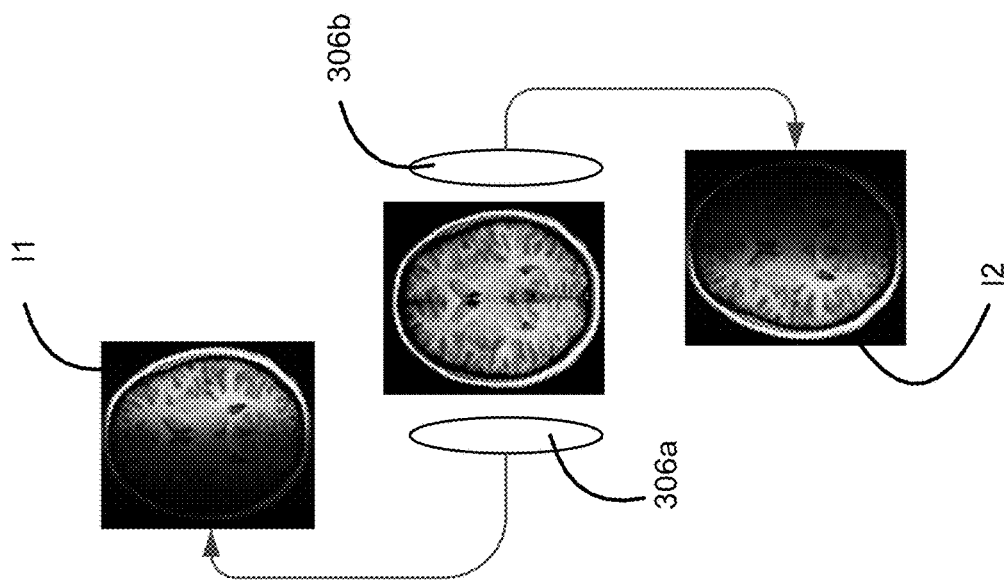
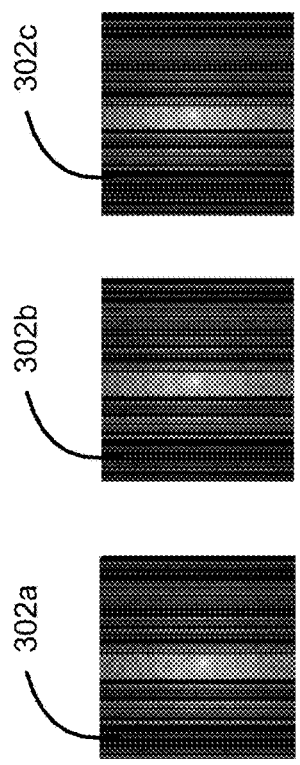
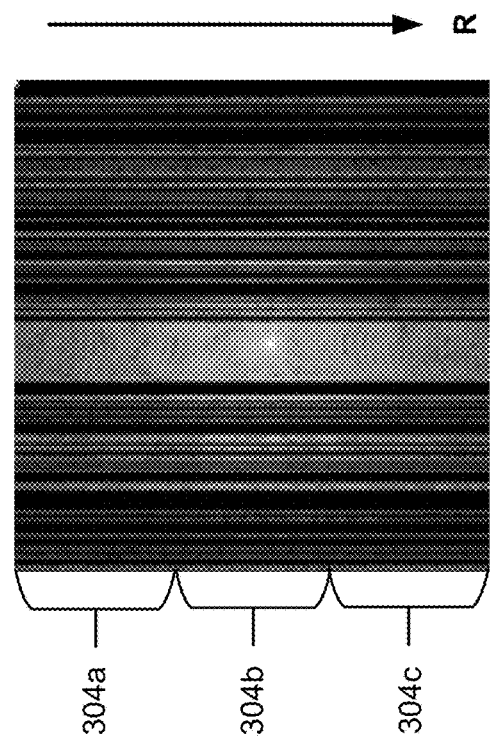

ate understanding of the examples disclosed
DEEP LEARNING BASED IMAGE RECONSTRUCTION

BACKGROUND

Multi-contrast MRI images of an anatomical structure such as the human brain or heart may provide useful information about the characteristics of the anatomical structure and are thus commonly used in clinical practice. The acquisition of high-resolution MRI images, however, requires large volumes of MRI data (e.g., k-space data) to be collected and encoded, and thus often results in long scan times and increased susceptibility to motion artifacts that may impact the image quality. To counter these issues, various acceleration techniques may be employed in the image acquisition process, for example, to under-sample the k-space data and reconstruct MRI images based on the under-sampled data. Conventional acceleration techniques such as compressed sensing (CS) based on methods, however, are often iterative and time-consuming, rendering them unsuitable for handling the large volume of data generated in a multi-dimensional setting (e.g., multiple contrasts, multiple coils, multiple slices, etc.) within a clinically acceptable timeframe.

Accordingly, systems, methods, and instrumentalities are highly desirable for reconstructing high resolution MRI images based on multi-dimensional MRI data and doing so under the requirements of clinical practice and limits of presently available hardware (e.g., GPU memory, processing speed, etc.).

SUMMARY

Described herein are systems, methods, and instrumentalities associated with reconstructing magnetic resonance (MR) images based on a set of under-sampled MR data (e.g., k-space data). The set of under-sampled MR data may be associated with an anatomical structure such as the human heart or brain, and may include data associated with multiple contrast settings, multiple coils, and a readout direction. The reconstruction of the MR images may be performed using deep learning based methods and/or by dividing the MR dataset into smaller portions or subsets. For example, a first MR image of the anatomical structure may be reconstructed using one or more neural networks based on a first portion of the under-sampled MR data that corresponds to a first subset of the multiple contrast settings, a first subset of the multiple coils, or a first segment in the readout direction. A second MR image of the anatomical structure may be reconstruct using the one or more neural networks based on a second portion of the under-sampled MR data that corresponds to a second subset of the multiple contrast settings, a second subset of the multiple coils, or a second segment in the readout direction. The first and second MR images may then be combined to obtain a desired MR image with multi-contrast properties or characteristics.

In examples, the first MR image may be reconstructed independently from the second MR image (e.g., the two MR images may be reconstructed in parallel). In examples, the second MR image is reconstructed based on the first MR image (e.g., in a sequential manner) to utilize the information encompassed in the first MR image. The first and second portions of the under-sampled MR data may be selected based on different criteria. For example, the first and second portions of the MR data may be associated with different contrast settings, or a same contrast setting but different coils, or the same contrast setting and coil but different segments in the readout direction.

In examples, the one or more neural networks may comprise a cascade convolutional neural network (CNN) that includes one or more data consistency layers. In examples, the one or more neural networks may comprise a plurality of depthwise separable convolutional layers. In examples, the one or more neural networks may each have a structure that is determined via a neural architecture search.

BRIEF DESCRIPTION OF THE DRAWINGS

A more detailed understanding of the examples disclosed herein may be obtained from the following description, given by way of example in conjunction with the accompanying drawing.

FIGS. 3A, 3B and 3C are block diagrams illustrating example ways for selecting subsets of MR data from a multi-dimensional MR dataset for purposes of reconstructing MR images in accordance with one or more embodiments described herein.

DETAILED DESCRIPTION

The present disclosure is illustrated by way of example, and not by way of limitation, in the figures of the accompanying drawings.

Figure 1:
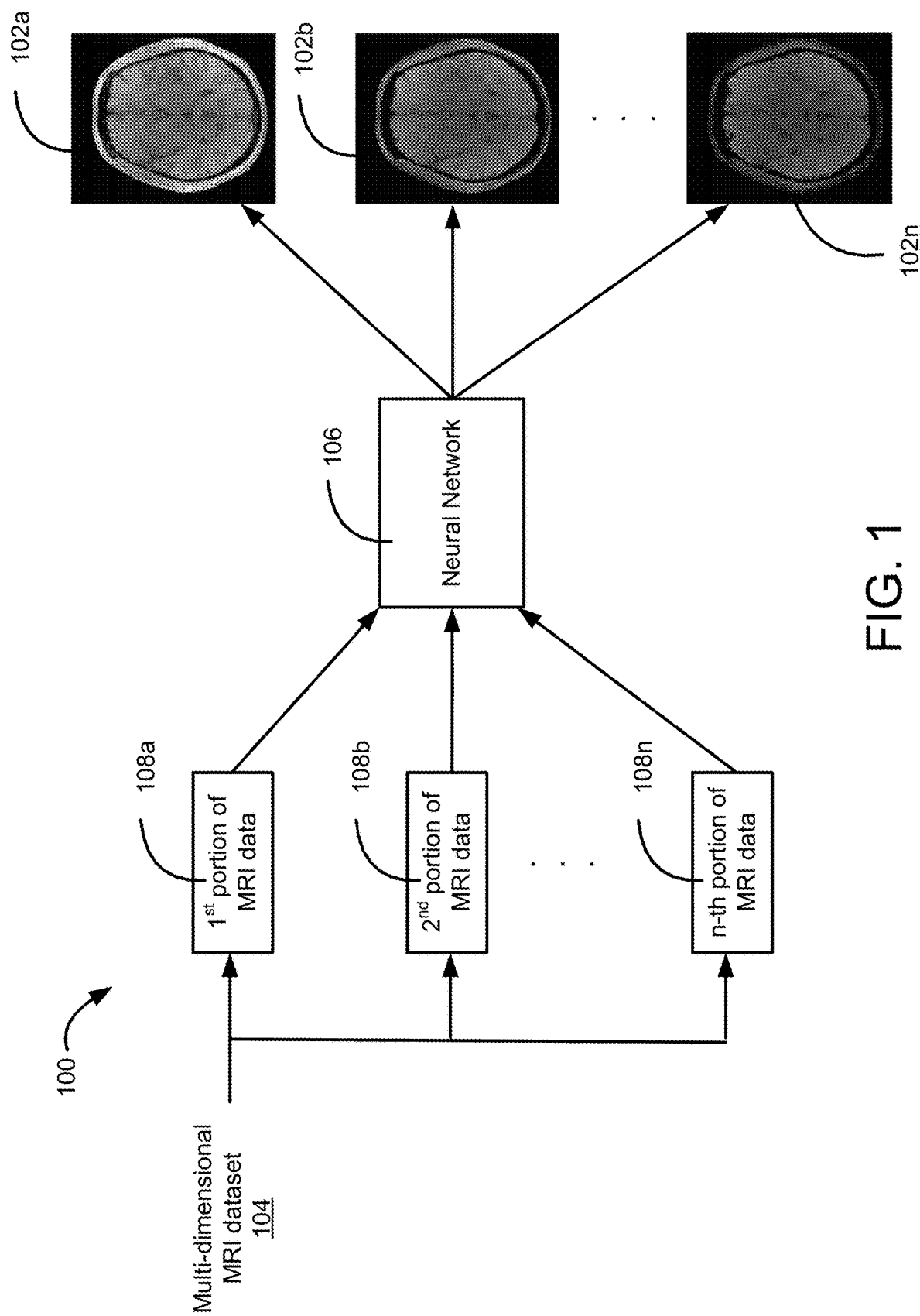
FIG. 1 is a block diagram illustrating an example framework for reconstructing magnetic resonance (MR) images using deep learning based methods in accordance with one or more embodiments described herein.

FIG. 1 is a block diagram illustrating an example framework 100 for reconstructing magnetic resonance (MR) images (e.g., 102a-n shown in the figure) of an anatomical structure (e.g., the human heart, brain, etc.) based on a multi-dimensional MR dataset 104 collected via an magnetic resonance imaging (MRI) device. As such, the multi-dimensional MR dataset 104 may include k-space data that represents the spatial frequency and/or phase information of the anatomical structure being scanned. It should be noted that, when used herein, the term multi-dimensional may refer to not only positions and/or directions in time and space (e.g., two-dimensional (2D), three-dimensional (3D), 2D/3D plus time, etc.), but also settings, elements, components, parameters, characteristics, factors, etc. that make up a complete entity. For example, a multi-dimensional MR dataset such as the multi-dimensional MR dataset 104 shown in FIG. 1 may mean not only that the dataset may include 2D or 3D MR data, but also that the data may encompass multiple contrast settings, multiple coils, multiple segments along a readout direction or a phase encoding direction, and/or the like.

The multi-dimensional MR dataset 104 may be collected from a single scan or multiple scans, and may include multiple slices obtained along a specific axis (e.g., a vertical or horizontal axis). Since the dataset 104 may encompass multiple dimensionalities (e.g., multiple contrasts, multiple coils, etc.), the amount of data may become too large to process within a reasonable time, if fully sampled. Therefore, in one or more of the embodiments described herein, the multi-dimensional MR dataset 104 may correspond to under-sampled MR data (e.g., under-sampled k-space data) obtained using various sub-sampling techniques (e.g., for purposes of accelerating the scan and/or image reconstruction operations), and the MR images 102a-n may be reconstructed based on the under-sampled MR data using a deep learning (DL) model learned by a neural network 106. Examples of the sub-sampling techniques may include Cartesian sampling, radial sampling, spiral sampling, Poisson-disk sampling, etc.

With some clinical applications, even under-sampled MR data may be impractical to process given the limitations of presently available hardware (e.g., processor speed, graphical processing unit (GPU) memory, etc.) and/or requirements of the clinical applications (e.g., shorter scan times, higher quality images, etc.). As such, in one or more of the embodiments described herein, the MR images 102a-n may be reconstructed based on respective portions or subsets of the multi-dimensional MR dataset 104. For example, the MR image 102a may be reconstructed based on a first portion 108a of the multi-dimensional MR dataset 104 that corresponds to a first subset of contrast settings, a first subset of coils, and/or a first segment in a readout direction, the MR image 102b may be reconstructed based on a second portion 108b of the multi-dimensional MR dataset 104 that corresponds to a second subset of contrast settings, a second subset of coils, and/or a second segment in the readout direction, and the MR image 102n may be reconstructed based on a n-th portion 108n of the multi-dimensional MR dataset 104 that corresponds to a n-th subset of contrast settings, a n-th subset of coils, and/or a n-th segment in the readout direction.

The portions (or subsets) of the multi-dimensional MR dataset 104 used to reconstruct the MR images 102a-n may be selected based on a combination of the dimensionalities described herein. For example, each of the MR data portions 108a-108n shown in FIG. 1 may correspond to a respective contrast setting (e.g., a subset of one or more contrast settings), a respective coil (e.g., a subset of one or more coils), a respective segment (e.g., a subset of one or more segments) along a readout direction, and/or the like. As another example, the MR data portions 108a-n may correspond to a same contrast setting (e.g., a same subset of contrast settings) but different coils (e.g., different subsets of coils) and/or different segments along the readout direction. As yet another example, the MR data portions 108a-n may correspond to a same contrast setting (e.g., a same subset of contrast settings) and a same coil (e.g., a same subset of coils), but different segments along the readout direction. As yet another example, the MR data portions 108a-n may correspond to a same contrast setting (e.g., a same subset of contrast settings) and a same segment (e.g., a same subset of segments) in the readout direction, but different coils (e.g., different subsets of coils). Other combinations of dimensionalities are also contemplated herein. But for ease of description, they are not all listed individually herein.

The portions (or subsets) 108a-n of the multi-dimensional MR dataset 104 may be selected (e.g., identified) from the multi-dimensional MR dataset 104 based on dimensions and/or sections of the multi-dimensional MR dataset 104, and/or various indicators (e.g., markers, tags, and/or other types of identifiers) that may be comprised in the multi-dimensional MR dataset 104. For example, the portion of the MR data that correspond to a specific contrast setting may be marked in the multi-dimensional MR dataset 104 by a unique identifier corresponding to the contrast setting, so that portion of the MR data may be selected from the multi-dimensional MR dataset 104 based on the unique identifier.

By reconstructing the MR images 102a-n based on respective portions (or subsets) of the multi-dimensional MR dataset 104 or training a neural network using portions (or subsets) of a large MR dataset, the framework described herein may allow for processing large volumes of data generated by multi-contrast, high resolution MRI procedures while at the same time alleviate the constraints imposed by presently available hardware. For example, the GPU(s) used to implement the neural network 106 may have a limited amount of memory and thus may not be able to accommodate an entire multi-dimensional MR dataset during training or testing/inference. By breaking the multi-dimensional MR dataset 104 into smaller portions that correspond to subsets of contrast settings, coils, and/or readout segments, the MR dataset 104 may be processed using deep learning based techniques despite the aforementioned hardware limitations. The reconstruction speed of each individual MR image may also become faster as a result of having a smaller amount of data to process. The individual MR images may be reconstructed in parallel (e.g., independent of each other) and in a sequential manner. In the latter case, the reconstruction of a second MR image (e.g., based on a second subset of MR data) may utilize features and/or characteristics of a first MR image reconstructed before the second MR image (e.g., using a first subset of MR data).

Figure 2:
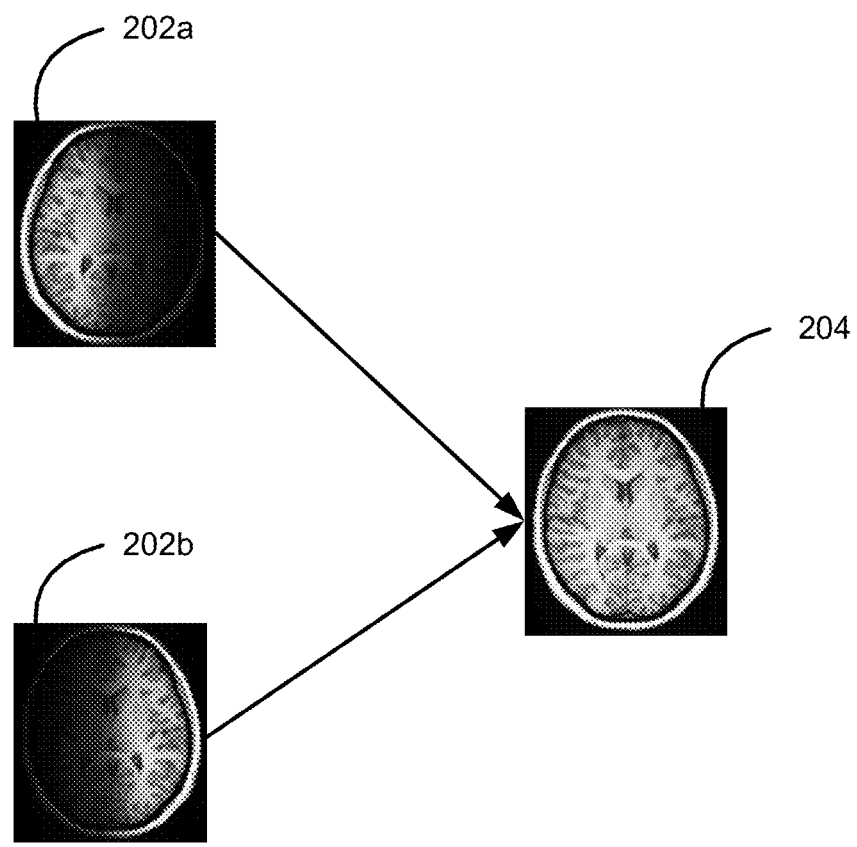
FIG. 2 is a block diagram illustrating an example of combining two individually reconstructed MR images to obtain a target MR image with desired characteristics in accordance with one or more embodiments described herein.

The MR images 102a-n generated using the techniques described herein may be combined to derive images (e.g., 2D images, 3D images, 2D or 3D plus time images, etc.) that have certain desired features, tissue contrasts, intensities, etc. FIG. 2 shows an example in which two images 202a and 202b reconstructed based on data collected respectively from two coils are combined into a target image 204 that encompasses information from both of the images 202a and 202b. Various techniques may be employed to combine the individually reconstructed MR images and/or to determine diagnostic metrics based on the individually reconstructed MR images and/or a combined MR image. For example, a composite proton density weighted (PDW) image and/or a T1 weighted (T1 W) image may be generated by averaging all or a subset of the MR images 102a-n shown in FIG. 1. As another example, a T2* mapping may be calculated by applying multi-dimensional integration (MDI) to the MR images 102a-n. As yet another example, one or more field maps may be extracted from the MR images 102a-n and used to generate a quantitative susceptibility mapping (QSM) (e.g., using a L2-norm optimization method with dynamic streaking artifact regularization).

FIGS. 3A-3C illustrate example ways for selecting a portion (or subset) of a large MR dataset to reconstruct an MR image. The example in FIG. 3A shows that an MR dataset may include data (e.g., k-space data) encompassing different contrast settings 302a-302c, and an MR image may be reconstructed based on a portion of the MR dataset that corresponds to one or more of the contrast settings 302a-

302c. Similarly, the example in FIG. 3B shows that an MR dataset may include data (e.g., k-space data) collected along a readout direction R, and an MR image may be reconstructed based on a portion of the MR dataset that corresponds to one or more segments (e.g., 304a, 304b, and 304c) along the readout direction R. Lastly, the example in FIG. 3C shows that an MR dataset may include data (e.g., k-space data) collected using multiple coils (e.g., 306a and 306b), and an MR image (e.g., I1, 12, etc.) may be reconstructed based on a portion of the MR dataset that corresponds to one or more of the coils (e.g., 306a and/or 306b). It should be noted that even though FIG. 3A-3C show portions of MR data being selected based on only one of contrast settings, readout segments, or coils, the figures should not be interpreted as limiting the ways in which the portions of MR data may be selected. Rather, as explained above, a multi-dimensional MR dataset may be divided into smaller portions or subsets for purposes of reconstructing corresponding MR images based on a combination of dimensionalities including a combination of contrast settings, readout segments, and/or coils.

Figure 4:
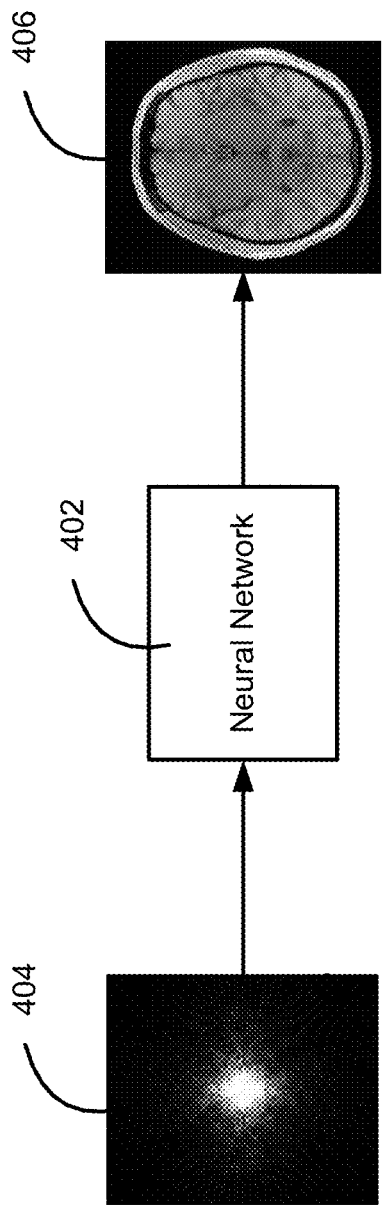
FIG. 4 is a block diagram illustrating an example of MR image reconstruction using an artificial neural network in accordance with one or more embodiments described herein.

FIG. 4 illustrates an example of using deep learning (DL) methods to reconstruct an MR image based on under-sampled, multi-contrast, multi-coil MR data (e.g., 2D or 3D MR data). As shown, the reconstruction may be performed using an artificial neural network (ANN) 402. The input 404 to the ANN may be a multi-dimensional, under-sampled MR dataset such as the multi-dimensional MRI dataset 104 shown in FIG. 1. The input 404 to the ANN may also be a portion or a subset of a multi-dimensional, under-sampled MR dataset such as the subset of MR data 108a, 108b, ... or 108n shown in FIG. 1. As explained herein, the multi-dimensional, under-sampled MR dataset may include data collected across multiple contrast settings, multiple coils, etc. Accordingly, when a subset of the MR dataset is used for reconstruction, the subset of MR data may be selected from the multi-dimensional, under-sampled MR dataset based on one or a combination of the contrast settings, coils, etc. In either case (e.g., whether an entire MR dataset or a portion of the MR dataset is provided as input to the ANN 404 at an inference time (e.g., once the ANN is trained and brought online)), the ANN 402 may be trained using portions or subsets of a multi-dimensional MRI dataset to learn a model for reconstructing MR images based on multi-dimensional MR data. For example, during the training, a multi-dimensional (e.g., multi-contrast, multi-coil) MRI training dataset may be divided into smaller portions each corresponding a specific contrast setting, coil, and/or segment along a readout direction (e.g., the segmentation may be performed randomly). The smaller portions of MR data may then be provided to the ANN 402 to reconstruct MR images that correspond to the specific contrast setting, coil, and/or segment (e.g., to avoid loading the entire dataset into GPU memory). This way, constraints imposed by hardware limitations such as limited GPU memories may be overcome, and once the ANN 402 is properly trained (e.g., offline), it may take only a forward pass to generate a reconstructed MR image based on under-sampled MR data (e.g., an entire multi-dimensional dataset or a portion thereof), resulting in a faster processing speed compared to conventional image reconstruction methods (e.g., CS-based methods).

It should be noted that even though the input 404 to the neural network 402 is shown in FIG. 4 as comprising an under-sampled MR dataset (e.g., k-space data), the input 404 may also include an MR image derived from the under-sampled MR dataset, for example, by applying inverse Fourier transform to the MR dataset.

The training of the ANN 402 may be formulated as learning a function $f_{nn}$ based on a large dataset that maps under-sampled (e.g., zero-filled) MR data (e.g., k-space measurements) to one or more fully sampled MR images by minimizing a loss function, as illustrated below:

$$f_{nn}: x_z \to y^{min}_\theta (L(f_{nn}(x_z|\theta), y))$$

where $\hat{y} = f_{nn}(x_z|\theta)$ may represent an MR image reconstructed by the ANN 402 in a forward pass with parameters $\theta$ (e.g., weights of the ANN 402), y may represent a ground truth image, $x_z$ may represent under-sample MR data (e.g., k-space data), and L may represent a loss function. The ANN 402 may utilize various network architectures. For example, the ANN 402 may be implemented as a 2D convolutional neural network (CNN), a 3D CNN, a cascade CNN, a recurrent neural network (RNN), a generative adversarial network (GAN), and/or a combination thereof. In examples, the specific structure of the ANN 402 may be determined by conducting a neural architecture search (NAS) aimed at learning a network topology that may achieve the best performance (e.g., in terms of computational efficiency) in the image reconstruction task described herein. Such a search may be conducted using at least the following modules or components: a search space, a search algorithm (or optimization method), and an evaluation strategy. The search space may define the types of ANN that may be designed and optimized, the search strategy may dictate how to explore the search space, and the evaluation strategy may be used to evaluate the performance of a candidate ANN. Various methods may be utilized to sample the search space and find the architecture that produces the best performance. These methods may include, for example, random search, reinforcement learning, gradient descent, and/or the like.

In one or more suitable architectures for the ANN 402, the network may include a plurality of convolutional layers, one or more pooling layers, and/or one or more fully connected layers. In examples, each of the convolutional layers may include a plurality of convolution kernels or filters configured to extract specific features from an input image through one or more convolution operations (e.g., the input image may be obtained by applying inverse Fourier transform to a corresponding MR dataset such as $x_z$ in the equation above). In examples, the convolutional layers may include one or more depthwise separable convolutional layers (e.g., 3D depthwise separable convolutional layers) configured to perform convolutional operations on an input that comprises multiple separate channels corresponding to different interpretations or renditions of the input. For instance, the real and imaginary components of the input complex values may be transformed into two separate channels and provided to the network. Each input channel may then be convolved with respective filters, and the convolved outputs may be stacked together to derive a target output.

The convolution operations described herein (e.g., using regular or depthwise convolutional layers) may be followed by batch normalization and/or linear or non-linear activation, and the features extracted by the convolutional layers may be down-sampled through the one or more pooling layers (e.g., using a 2×2 window and a stride of 2) to reduce the redundancy and/or dimension of the features (e.g., by a factor of 2). As a result of the convolution and/or down-sampling operations, respective feature representations of the input image may be obtained, for example, in the form of one or more feature maps or feature vectors.

The ANN 402 may also include a plurality of transposed convolutional layers and/or one or more un-pooling layers. Through these layers, the ANN 402 may perform a series of up-sampling and/or transposed convolution operations based on the feature map(s) or feature vector(s) produced by the down-sampling operation described above. For example, the ANN 402 may up-sample (e.g., using 3×3 transposed convolutional kernels with a stride of 2) the feature representations based on pooled indices stored in the down-sampling stage to restore the features extracted from the input image to a size or resolution that corresponds to a fully sampled MR dataset or image (e.g., an MR dataset may be converted into an MR image and vice versa through Fourier transform).

Various loss functions may be employed to facilitate the training of the ANN 402. Such a loss function may be based on, for example, mean squared errors (MSE), L1-norm, L2-norm, a structural similarity index measure (SSIM) loss, an adversarial loss, and/or the like. The training data may be acquired from practical MRI procedures (e.g., 3D multi-contrast, multi-coil procedures) with parallel imaging to obtain ground truth images. The data may be under-sampled, for example, using 3× and/or 5× Poisson-disk under-sampling schemes in phase encoding and/or slice directions.

Figure 5:
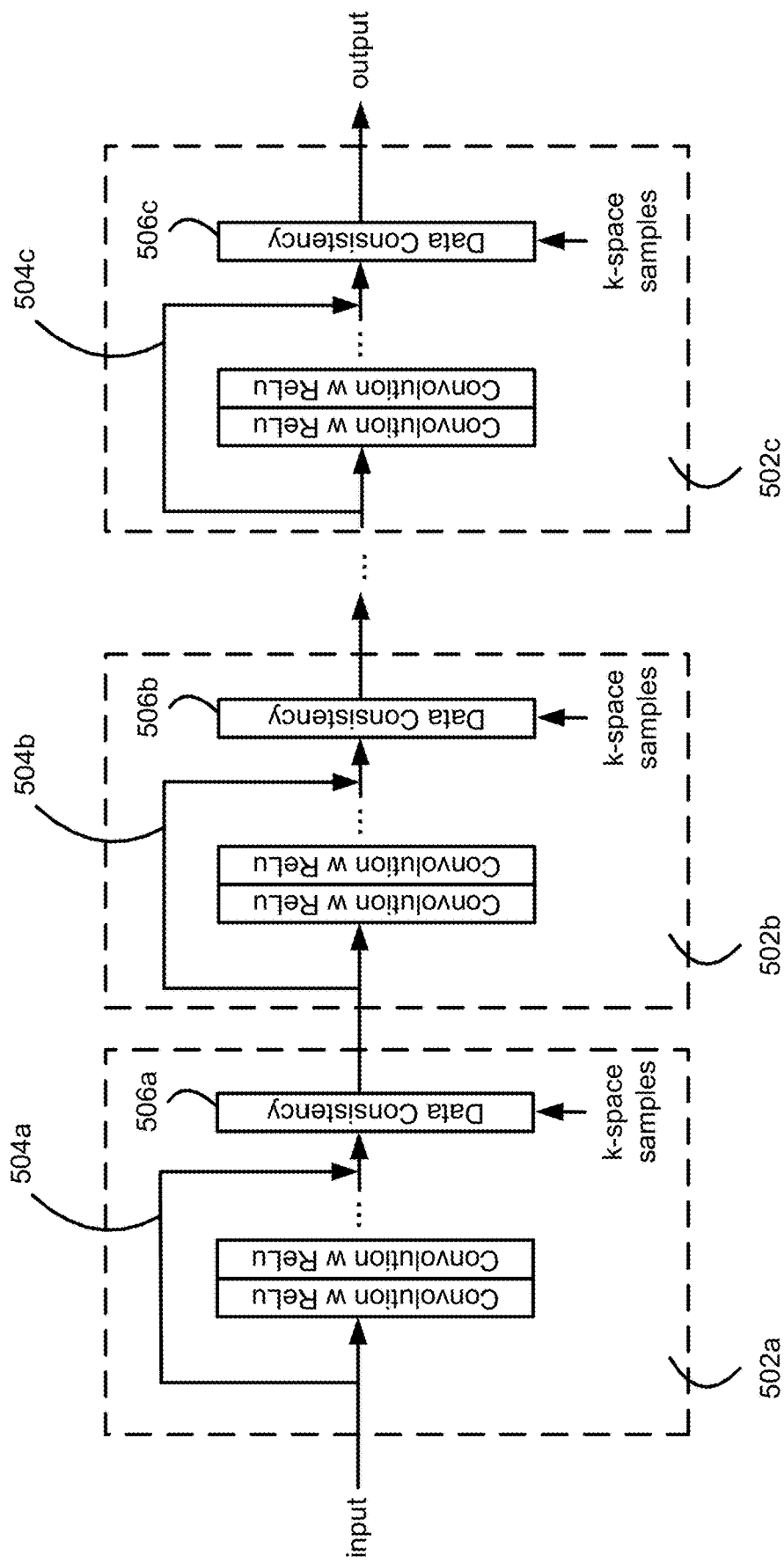
FIG. 5 is a block diagram illustrating an example neural network that may be used to reconstruct MR images based on under-sampled MR data in accordance with one or more embodiments described herein.

FIG. 5 illustrates an example cascade network structure that may be used to implement the ANN 402. As shown, the network may include a plurality of blocks (e.g., subnetworks) 502a-c each comprising one or more (e.g., five) convolutional layers (e.g., 2D or 3D convolutional layers), one or more pooling layers, and/or one or more batch normalization layers. One or more (e.g., each) of the convolutional layers may be associated with respective activation functions (e.g., rectified linear units (ReLU)), and each of the blocks or subnetworks 502b-c in the cascading structure that is positioned after the first block or subnetwork 502a may learn to reconstruct an MR image based on the output of a preceding block or subnetwork. The blocks or subnetworks 502a-c may be configured to perform residual learning (e.g., the network layers may be trained to learn a residual mapping with reference to the layer input(s)). As such, each of the blocks or subnetworks 502a-c may include a respective residual connection 504a-c configured to sum the output of the block or subnetwork to its input. All the blocks or subnetworks 502a-c may be trained jointly in an end-to-end manner as one large network.

One or more (e.g., all) of the blocks or subnetworks may also include respective data consistency layers 506a-c (e.g., data consistency functions or modules) configured to ensure that values predicted by a subnetwork or block in the image domain are consistent with acquired k-space samples. To that end, the operations performed by the data consistency layers 506a-c may include transforming (e.g., via a Fourier transform) an image reconstructed by a subnetwork or network block to k-space data and performing a comparison (e.g., element-wise comparison) of the network-predicted values with ground-truth k-space samples, etc.

Figure 6:
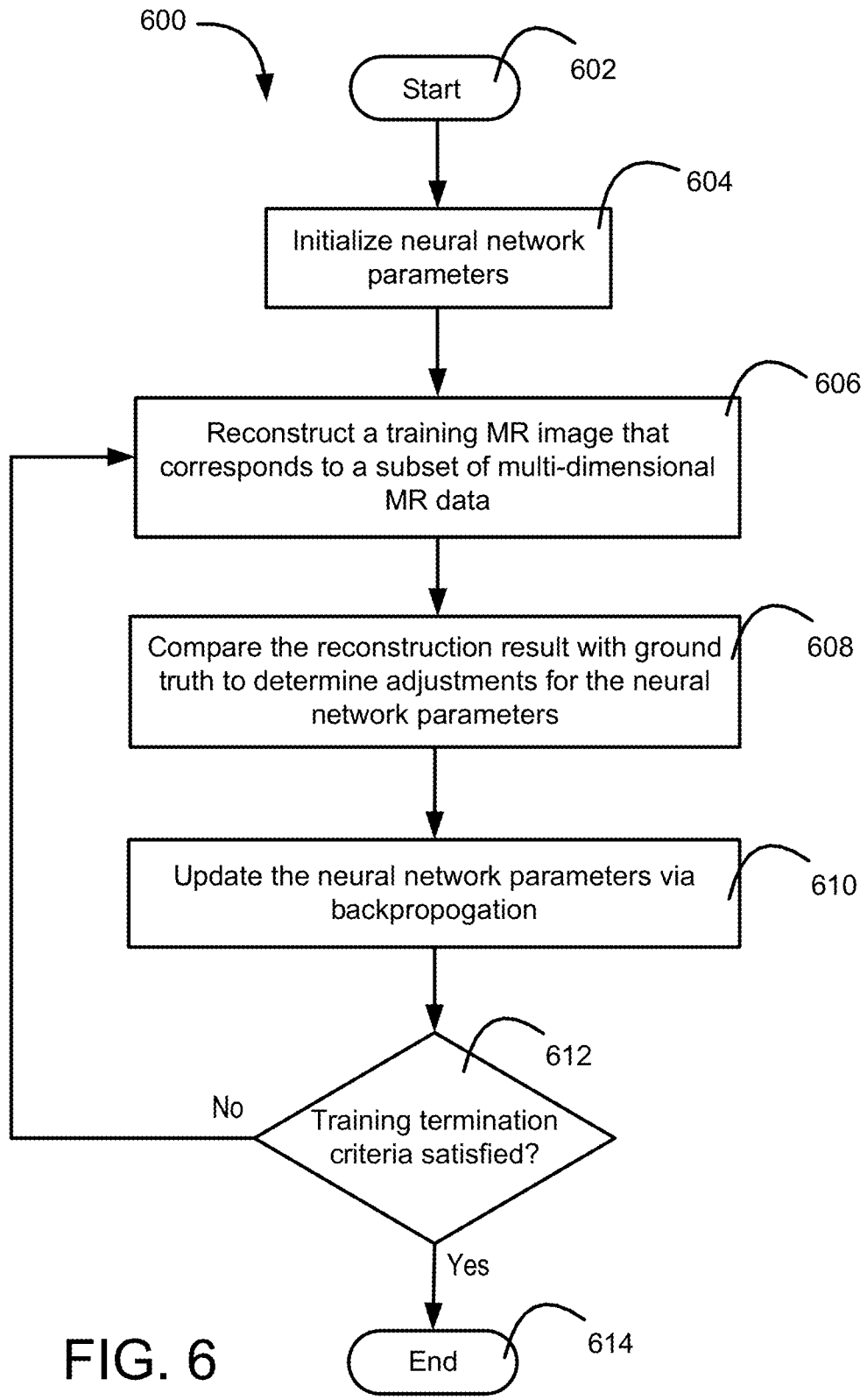
FIG. 6 is flow diagram illustrating an example process for training a neural network to perform the image reconstruction tasks described herein.

FIG. 6 illustrates an example process 600 for training a neural network (e.g., the ANN 402 shown in FIG. 4) to perform the image reconstruction operations described herein. The training may be performed using data collected from practical MRI procedures (e.g., 3D multi-contrast, multi-coil MRI procedures) with parallel imaging to obtain ground truth images. The training data may then be retrospectively under-sampled, for example, using 3× and/or 5× Poisson-disk under-sampling schemes in phase encoding and/or slice directions to obtain an under-sampled training dataset encompassing multiple contrasts and multiple coils. The under-sampled training dataset may be further divided into smaller portions (e.g., subsets) each corresponding a specific set of one or more contrast settings, one or more coils, and/or one or more segments along a readout direction (e.g., the readout may be randomly cropped into 128 segments for training purposes). The smaller portions or subsets of the training dataset may then be to train the neural network to learn a model for reconstructing MR images based on under-sampled data (e.g., k-space data).

The process 600 may start at 602 and, at 604, initial parameters of the neural network (e.g., weights associated with various filters or kernels of the neural network) may be initialized. The parameters may be initialized, for example, based on samples collected from one or more probability distributions or parameter values of another neural network having a similar architecture. At 606, the neural network may receive an input MR image associated with a portion or subset of the MR data described herein (e.g., the input MR image may be generated by applying inverse Fourier transform to the input MR data), and reconstruct an output image through various layers of the neural network. At 608, the reconstructed image may be compared to a ground truth image to determine adjustments that need to be made to the presently assigned neural network parameters. The adjustments may be determined based on a loss function (e.g., MSE, L1, L2, etc.) and a gradient descent (e.g., a stochastic gradient decent) associated with the loss function.

At 610, the neural network may apply the adjustments to the presently assigned network parameters, for example, through a backpropagation process. At 612, the neural network may determine whether one or more training termination criteria are satisfied. For example, the neural network may determine that the training termination criteria are satisfied if the neural network has completed a predetermined number of training iterations, if the difference between the prediction result and a ground truth value is below a predetermined threshold, or if the change in the value of the loss function between two training iterations falls below a predetermined threshold. If the determination at 612 is that the training termination criteria are not satisfied, the neural network may return to 606. If the determination at 612 is that the training termination criteria are satisfied, the neural network may end the training process 600 at 614.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process the are depicted and described herein, and not all illustrated operations are required to be performed.

Figure 7:
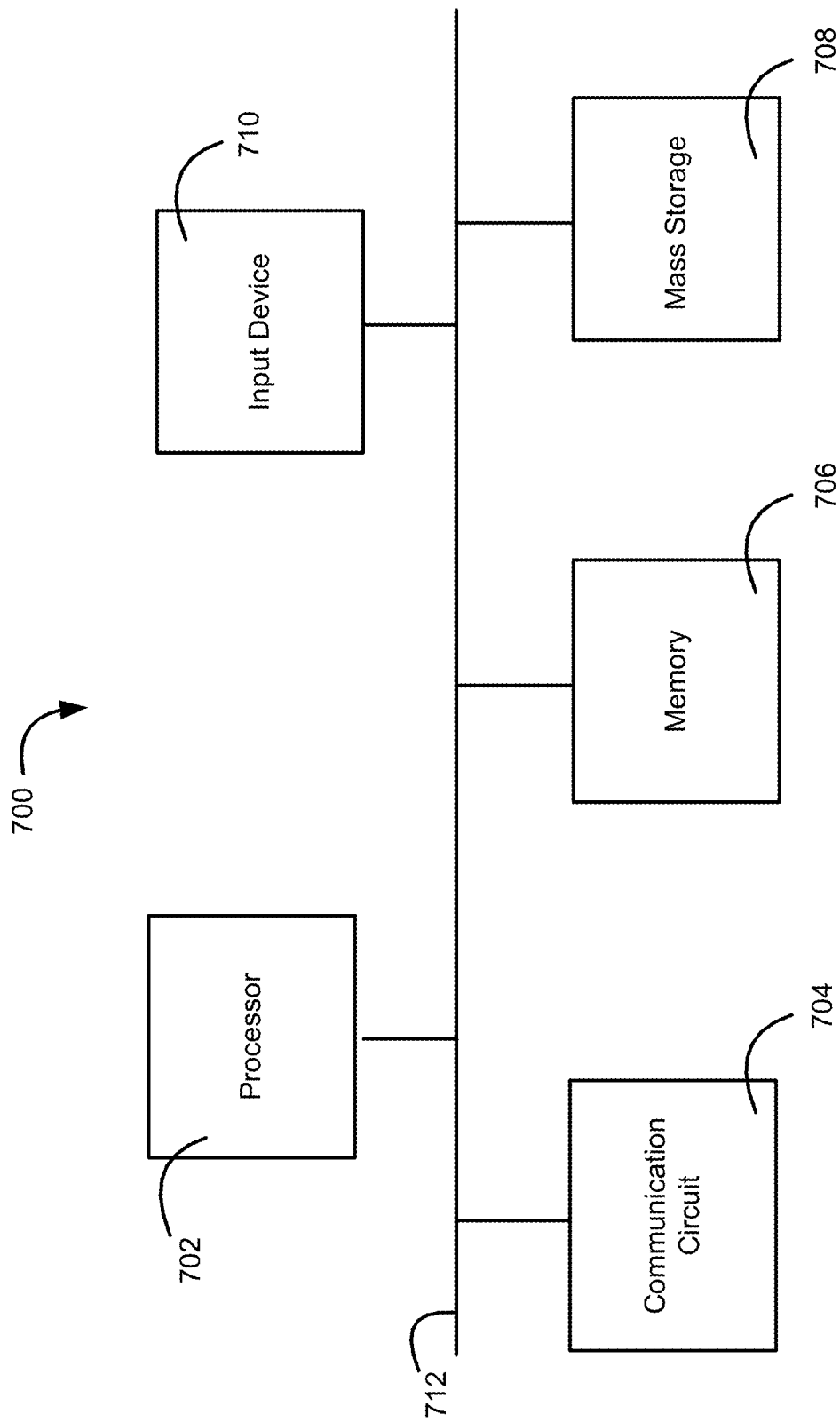
FIG. 7 is a block diagram illustrating example components of an apparatus that may be used to perform the image reconstruction tasks described herein.

The systems, methods, and/or instrumentalities described herein may be implemented using one or more processors, one or more storage devices, and/or other suitable accessory devices such as display devices, communication devices, input/output devices, etc. FIG. 7 is a block diagram illustrating an example apparatus 700 that may be configured to perform the image reconstruction operations described herein. As shown, the apparatus 700 may include a processor (e.g., one or more processors) 702, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The apparatus 700 may further include a communication circuit 704, a memory 706, a mass storage device 708, an input device 710, and/or a communication link 712 (e.g., a communication bus) over which the one or more components shown in the figure may exchange information.

The communication circuit 704 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 706 may include a storage medium (e.g., a non-transitory storage medium) configured to store machine-readable instructions that, when executed, cause the processor 702 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 708 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 702. The input device 710 may include a keyboard, a mouse, a voice-controlled input device, a touch sensitive input device (e.g., a touch screen), and/or the like for receiving user inputs to the apparatus 700.

It should be noted that the apparatus 700 may operate as a standalone device or may be connected (e.g., networked or clustered) with other computation devices to perform the functions described herein. And even though only one instance of each component is shown in FIG. 7, a skilled person in the art will understand that the apparatus 700 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A method of reconstructing magnetic resonance (MR) images, the method comprising:
   obtaining an under-sampled MR dataset associated with an anatomical structure, wherein the under-sampled MR dataset is associated with a single MR scan and includes data associated with multiple contrast settings, multiple coils, and multiple segments in a readout direction;
   determining a first portion of the under-sampled MR dataset that corresponds to a first target contrast, wherein the first portion of the under-sampled MR dataset includes data associated with a first subset of the multiple coils and a first segment in the readout direction;
   reconstructing, using one or more neural networks, a first MR image of the anatomical structure based on the first portion of the under-sampled MR dataset;
   determining a second portion of the under-sampled MR dataset that corresponds to the first target contrast, wherein the second portion of the under-sampled MR dataset includes data associated with a second subset of the multiple coils and a second segment in the readout direction;
   reconstructing, using the one or more neural networks, a second MR image of the anatomical structure based on the second portion of the under-sampled MR dataset; and
   deriving an MR image of the anatomical structure that is associated with the first target contrast based at least on the first MR image and the second MR image.

2. The method of claim 1, wherein the first MR image is reconstructed independently from the second MR image.

3. The method of claim 1, wherein the first MR image and the second MR image are reconstructed sequentially, and wherein the second MR image is reconstructed based on the first MR image.

4. The method of claim 1, further comprising:
   determining a third portion of the under-sampled MR dataset that corresponds to a second target contrast, wherein the third portion of the under-sampled MR dataset includes data associated with a third subset of the multiple coils and a third segment in the readout direction;
   reconstructing, using the one or more neural networks, a third MR image of the anatomical structure based on the third portion of the under-sampled MR dataset;
   determining a fourth portion of the under-sampled MR dataset that corresponds to the second target contrast, wherein the fourth portion of the under-sampled MR dataset includes data associated with a fourth subset of the multiple coils and a fourth segment in the readout direction;
   reconstructing, using the one or more neural networks, a fourth MR image of the anatomical structure based on the fourth portion of the under-sampled MR dataset; and
   deriving an MR image of the anatomical structure that is associated with the second target contrast based at least on the third MR image and the fourth MR image.

5. The method of claim 4, wherein the MR image associated with the first target contrast and the MR image of the anatomical structure associated with the second target contrast are derived independently of each other.

6. The method of claim 1, wherein the one or more neural networks comprise a three-dimensional convolutional neural network (CNN).

7. The method of claim 1, wherein the one or more neural networks comprise a cascade of convolutional neural network (CNN) blocks, and wherein each CNN block is associated with a respective data consistency layer.

8. The method of claim 1, wherein the one or more neural networks comprise a plurality of three-dimensional depthwise separable convolutional layers.

9. The method of claim 1, wherein the under-sampled MR dataset comprises two-dimensional or three-dimensional MR data.

10. An apparatus, comprising:
one or more processors configured to:
obtain an under-sampled MR dataset associated with an anatomical structure, wherein the under-sampled MR dataset is a single MR scan and includes data associated with multiple contrast settings, multiple coils, and multiple segments in a readout direction;
determine a first portion of the under-sampled MR dataset that corresponds to a first target contrast, wherein the first portion of the under-sampled MR dataset includes data associated with a first subset of the multiple coils and a first segment in the readout direction;
reconstruct, using one or more neural networks, a first MR image of the anatomical structure based on the first portion of the under-sampled MR dataset;
determine a second portion of the under-sampled MR dataset that corresponds to the first target contrast, wherein the second portion of the under-sampled MR dataset includes data associated with a second subset of the multiple coils and a second segment in the readout direction;
reconstruct, using the one or more neural networks, a second MR image of the anatomical structure based on the second portion of the under-sampled MR data; and
derive an MR image of the anatomical structure that is associated with the first target contrast based at least on the first MR image and the second MR image.

11. The apparatus of claim 10, wherein the first MR image is reconstructed independently from the second MR image.

12. The apparatus of claim 10, wherein the first MR image and the second MR image are reconstructed sequentially, and wherein the second MR image is reconstructed based on the first MR image.

13. The apparatus of claim 10, wherein the one or more processors are further configured to:
determine a third portion of the under-sampled MR dataset that corresponds to a second target contrast, wherein the third portion of the under-sampled MR dataset includes data associated with a third subset of the multiple coils and a third segment in the readout direction;
reconstruct, using the one or more neural networks, a third MR image of the anatomical structure based on the third portion of the under-sampled MR dataset;
determine a fourth portion of the under-sampled MR dataset that corresponds to the second target contrast, wherein the fourth portion of the under-sampled MR dataset includes data associated with a fourth subset of the multiple coils and a fourth segment in the readout direction;
reconstruct, using the one or more neural networks, a fourth MR image of the anatomical structure based on the fourth portion of the under-sampled MR dataset; and
derive an MR image of the anatomical structure that is associated with the second target contrast based at least on the third MR image and the fourth MR image.

14. The apparatus of claim 13, wherein the MR image associated with the first target contrast and the MR image of the anatomical structure associated with the second target contrast are derived independently of each other.

15. The apparatus of claim 10, wherein the one or more neural networks comprise a three-dimensional convolutional neural network (CNN).

16. The apparatus of claim 10, wherein the one or more neural networks comprise a cascade of convolutional neural network (CNN) blocks, and wherein each CNN block is associated with a respective data consistency layer.

17. The apparatus of claim 10, wherein the one or more neural networks comprise a plurality of three-dimensional depthwise separable convolutional layers.

18. The apparatus of claim 10, wherein the under-sampled MR dataset comprises two-dimensional or three-dimensional MR data.

19. The apparatus of claim 10, wherein the one or more neural networks each have a structure determined via a neural architecture search.

20. A method of training a neural network to learn a model for reconstructing magnetic resonance (MR) images, the method comprising:
the neural network obtaining a first portion of a MR training dataset, wherein the MR training dataset is associated with a single MR scan and comprises under-sampled MR data associated with an anatomical structure, multiple contrast settings, multiple coils, and multiple segments in a readout direction, and wherein the first portion of the MR training dataset that corresponds to a target contrast and includes data associated with a first subset of the multiple coils and a first segment in the readout direction;
the neural network reconstructing a first MR image of the anatomical structure based on the first portion of the MR training dataset;
the neural network obtaining a second portion of the MR training dataset, wherein the second portion of the MR training dataset is associated with the target contrast and includes data associated with a second subset of the multiple coils and a second segment in the readout direction;
the neural network reconstructing a second MR image of the anatomical structure based on the second portion of the MR training dataset;
the neural network deriving an MR image of the anatomical structure that is associated with the target contrast based at least on the first MR image and the second MR image; and
the neural network adjusting one or more operating parameters based on a difference between the derived MR image and a ground truth MR image.

* * * * *